United States Patent
Vogel et al.

(10) Patent No.: US 11,927,651 B2
(45) Date of Patent: Mar. 12, 2024

(54) SYSTEM FOR THE ONE-SIDED GENERATION OF MAGNETIC FIELDS FOR THE MULTIDIMENSIONAL ENCODING OF MAGNETIC PARTICLES AND METHOD OF OPERATION THEREOF

(71) Applicant: Julius-Maximilians-Universität Würzburg, Würzburg (DE)

(72) Inventors: Patrick Vogel, Gerbrunn (DE); Martin Rückert, Reichenberg (DE)

(73) Assignee: Julius-Maximilians-Universität Würzburg, Würzburg (DE)

( * ) Notice: Subject to any disclaimer, the term of this patent is extended or adjusted under 35 U.S.C. 154(b) by 276 days.

(21) Appl. No.: 17/431,962

(22) PCT Filed: Feb. 21, 2020

(86) PCT No.: PCT/EP2020/054584
§ 371 (c)(1),
(2) Date: Aug. 18, 2021

(87) PCT Pub. No.: WO2020/173819
PCT Pub. Date: Sep. 3, 2020

(65) Prior Publication Data
US 2022/0163607 A1 May 26, 2022

(30) Foreign Application Priority Data
Feb. 28, 2019 (EP) .................................. 19159986

(51) Int. Cl.
*G01R 33/12* (2006.01)
*A61B 5/0515* (2021.01)
*G01R 33/00* (2006.01)

(52) U.S. Cl.
CPC ........ *G01R 33/1276* (2013.01); *A61B 5/0515* (2013.01); *G01R 33/0094* (2013.01)

(58) Field of Classification Search
CPC ............ G01R 33/1276; G01R 33/0094; A61B 5/0515
See application file for complete search history.

(56) References Cited

U.S. PATENT DOCUMENTS

2013/0157256 A1* 6/2013 Rueckert .................. C12Q 1/04
435/7.1
2015/0160312 A1 6/2015 Weinberg
(Continued)

FOREIGN PATENT DOCUMENTS

WO 2013088413 A1 6/2013

OTHER PUBLICATIONS

Can Baris Top et al., Electronically Rotated and Translated Field Free Line Generation for Open Bore Magnetic Particle Imaging, Research Article. ASELSAN Research Center, Ankara, Turkey, 06370, 36 pages.
(Continued)

*Primary Examiner* — Jermele M Hollington
*Assistant Examiner* — Taqi R Nasir
(74) *Attorney, Agent, or Firm* — Grossman, Tucker, Perreault & PFleger, PLLC; Steven J. Grossman

(57) ABSTRACT

A system for one-sided measuring a presence of magnetic particles in a probe volume comprises a one-sided coil assembly and a current controller, wherein the one-sided coil assembly is arranged around a central coil assembly axis for generating a rotating magnetic field distribution and comprises at least 3, preferably at least 4, circumferentially distributed coil assembly sectors, wherein the current controller is configured to generate a time varying current in each of said coil assembly sectors, said time varying current comprising a periodic modulation with a rotation frequency and phase shifted between adjacent coil assembly sectors to generate a magnetic field rotating in a plane perpendicular to (Continued)

the coil assembly axis, said magnetic field rotating with a rotation frequency associated with a frequency of said periodic modulation, and wherein the system is configured for measuring said presence of magnetic particles in said probe volume with said one-sided coil assembly.

20 Claims, 7 Drawing Sheets

(56) References Cited

U.S. PATENT DOCUMENTS

| | | | |
|---|---|---|---|
| 2015/0300987 A1* | 10/2015 | Rahmer | G01N 27/72 |
| | | | 324/239 |
| 2016/0313420 A1 | 10/2016 | Rasche et al. | |
| 2017/0067972 A1 | 3/2017 | Diamond et al. | |
| 2018/0231629 A1* | 8/2018 | Top | G01R 33/1276 |

OTHER PUBLICATIONS

Gleich & Weizenecker, Tomographic Imaging Using the Nonlinear Response of Magnetic Particles, Nature, Jun. 30, 2005, p. 1214-1217, vol. 435, Nature Publishing Group, Germany.

Ksenija Grafe et al., 2D Images Recorded With A Single-Sided Magnetic Particle Imaging Scanner, IEEE Transactions On Medical Imaging, Dec. 2015, DOI: 10.1109/TMI.2015.2507187.

Ksenija Grafe et al., First Phantom Measurements With A 3D Single-Sided MPI Scanner, Book of Abstracts, 2018, pp. 201-202, Institute Of Medical Engineering, University of Lubeck.

Knopp et al., Magnetic Particle Imaging: From Proof of Principle to Preclinical Applications, IOPScience, 2017, Institute of Physics and Engineering in medicine, Author submitted manuscript-PMB-105354.R1, 58 pages.

Timo F. Sattel et al., Single-Sided Device for Magnetic Particle Imaging, Journal of Physics D: Applied Physics, Dec. 11, 2008, vol. 42, IOP Publishing, DOI: 10.1088/0022-3727/42/2/022001.

Alexey Tonyushkin, Single-Sided Field Free Line Generator Magnet For Multidimensional Magnetic Particle Imaging, Jan. 13, 2007, 7 pages.

Alexey Tonyushkin, Single-Sided Hybrid Selection Coils For Field-Free Line Magnetic Particle Imaging, International Journal on Magnetic Particle Imaging, Mar. 23, 2017, vol. 3, No. 1, Article ID 1703009, Infinite Science Publishing.

Juergen Weizenecker et al., Magnetic Particle Imaging Using A Field Free Line, Journal of Physics D; Applied Physics, May 1, 2008, vol. 41, IOP Publishing, Germany.

Juergen Weizenecker et al., Three-Dimensional Real-Time in Vivo Magnetic Particle Imaging, Physics in Medicine and Biology, Feb. 10, 2009, vol. 54, IOP Publishing, Germany.

International Search Report and Written Opinion of International Application No. PCT/EP2020/054584, dated May 19, 2020, 20 pages.

Yoshida et al: Magnetic fluid dynamics in a rotating magnetic field:, Journal of Applied Physics, US, vol. 111, No. 5, Mar. 1, 2012, pp. 53901-53901.

Dieckhoff, Jan et al: "Fluxgate based detection of magnetic nanoparticle dynamics in a rotating magnetic field", Applied Physics Letters, A I P Publishing LLC, US, vol. 99, No. 11, Sep. 12, 2011, pp. 112501-112501.

Timo F. Sattel et al: "Fast Track Communication: Single-sided device for magnetic particle imaging", Journal of Physics D: Applied Physics, Institute of Physics Publishing Ltd, GB, vol. 42, No. 2, Jan. 21, 2009, p. 22001-22001.

* cited by examiner

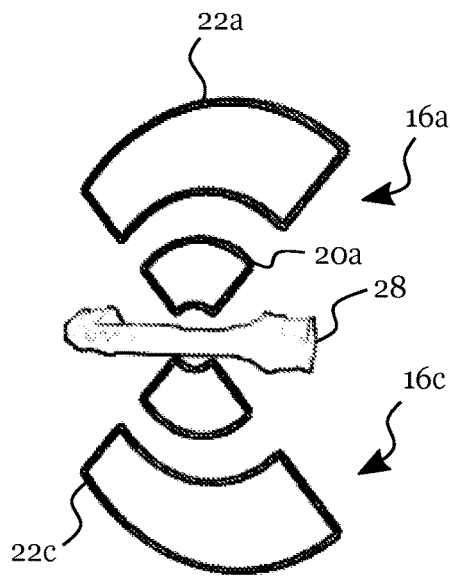
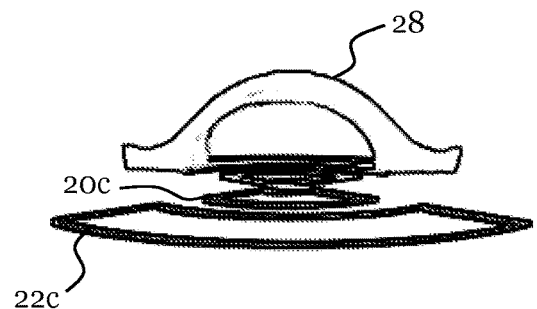
Fig. 4A
Fig. 4B
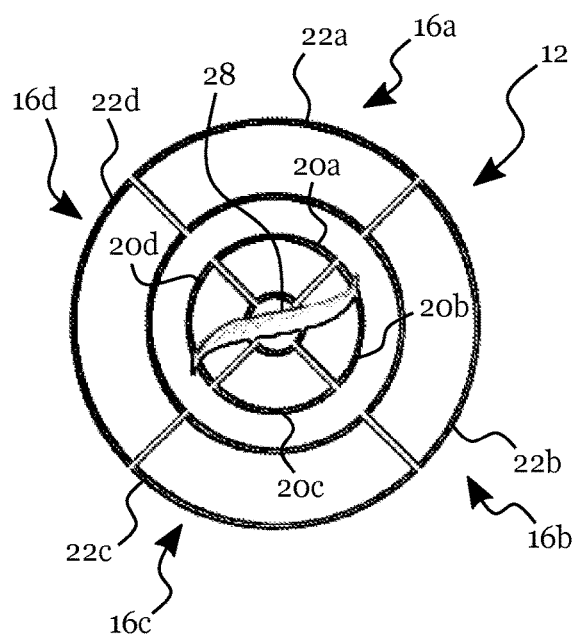
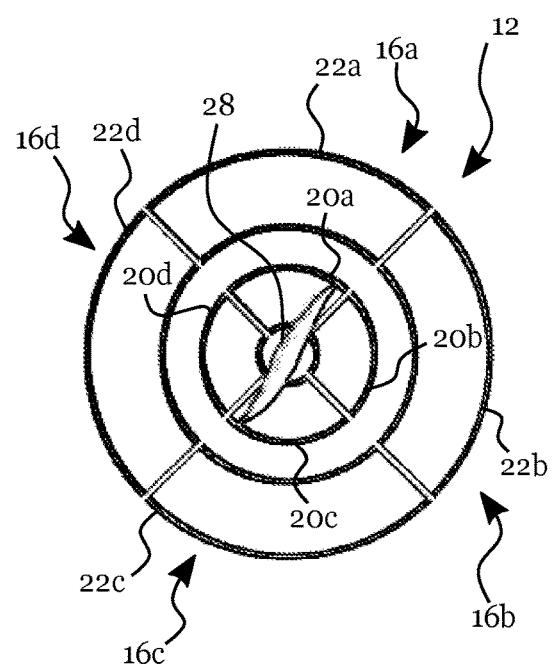
Fig. 4C
Fig. 4D

SYSTEM FOR THE ONE-SIDED GENERATION OF MAGNETIC FIELDS FOR THE MULTIDIMENSIONAL ENCODING OF MAGNETIC PARTICLES AND METHOD OF OPERATION THEREOF

RELATED APPLICATIONS

This application is a National Phase Application of International PCT Application No. PCT/EP2020/054548 filed Feb. 21, 2020, which claims priority to European Application No. EP19159986.9 filed Feb. 28, 2019, both of which are fully incorporated herein by reference.

FIELD OF THE INVENTION

The present invention is in the field of magnetic imaging technology. More precisely, the present invention relates to magnetic particle imaging with one-sided coil assemblies.

BACKGROUND

The treatment and diagnosis of medical conditions increasingly relies on imaging technology. Commonly used methods such as X-ray Computed Tomography (CT) and Positron Emission Tomography (PET) provide short acquisition times with high spatial resolution but expose the patient to high-energy radiation.

In contrast, imaging technologies based on magnetic fields use the characteristic response of atoms, molecules or particles in the human body to a time varying magnetic field distribution to provide three-dimensional images of the patient's body. For example, nuclear magnetic resonance (NMR) uses the response of hydrogen atoms in the patient's body to microwave fields applied alongside magnetic field gradients to infer the concentration and the position of the hydrogen atoms in the patient's body and can be used to provide a three-dimensional image of the tissue composition of the patient.

Magnetic particle imaging (MPI) is an imaging technique which has been recently proposed by Gleich et al. ("*Tomographic imaging using the nonlinear response of magnetic particles*" in *Nature Letters*, June 2005) as a radiation-free diagnosis tool. In this technique, small magnetic particles, such as iron oxide particles with a diameter in a range of 10 to 40 nm, are introduced into the body of the patient and the response of these particles to time varying magnetic fields is used to infer their concentration and position. In particular, Gleich et al. proposed using a magnetic field free point (FFP) at which the magnetization of the particles can be switched with a low amplitude time-varying magnetic field giving rise to a non-linear response to the drive field, while outside of the magnetic FFP, the time-varying magnetic field does not produce any significant magnetization change. The non-linear response may thus be associated with the field free region. By moving the magnetic FFP within the probe volume and recording the magnetic response to said time-varying magnetic field, a three-dimensional image of the concentration of the small magnetic particles can be produced. By functionalizing the magnetic particles, even specific molecules or cells can be traced throughout the body of the patient. US 2018/0231629 A1 discloses a coil arrangement for generating a magnetic field free line (FFL) defining an extended field free region in an investigated probe volume, which is subsequently rotated as well as translated by modulating currents in opposing coil structures of a two-sided coil assembly to scan the probe volume with the FFL. Based on a nonlinear response of the particles at the field free line to a externally applied periodic drive field, the magnetic particle distribution and concentration may be inferred with image reconstruction schemes similar to the ones used in CT.

As an alternative or complementary magnetic imaging technique, DE102010013900 A1 teaches an imaging method based on a rotational drift of magnetic nanoparticles in a rotating magnetic field to infer a presence or distribution of magnetic particles in a sample. Depending on the strength and the frequency of the externally applied rotating field, (liquid suspended) magnetic particles in the probe volume will synchronously rotate with the external magnetic field up to a critical frequency, above which the response of the magnetic particles will become asynchronous, detectable as an off-frequency magnetization term, allowing the determination of the presence and properties of magnetic particles in an investigated probe volume ("Rotational drift spectroscopy"). The magnetic field dependence of the critical frequency of the magnetic particles allows spatially resolving the presence of magnetic particles in a probe volume by sequentially applying magnetic field gradients alongside the rotating magnetic field along different segmentation axes ("Rotational drift imaging").

However, the required field strengths for these approaches currently restrict the application in human-sized scanners due to a limitation of the probe volume by the required field strengths and accordingly a sample size due to the coil geometries surrounding the investigated sample in traditional systems.

These limitations could be at least partially circumvented with one-sided scanner assemblies in which the probe volume is not confined by the coil structure, and which may therefore allow localized measurements of an extended sample, e.g. selected body parts.

Gräfe et al. ("*First Phantom Measurement with a 3D single-sided MPI scanner*" Book of abstracts, p. 201, IWMPI 2018) recently showed the possibility to use single sided coil assemblies for 3D scanning of a probe volume above the scanner with a field free point. The assembly uses concentrically aligned coils to define the field free point and D-shaped deflection coils to displace the FFP and accordingly scan a probe volume.

Tonyushkin ("Single-Sided Field-Free Line Generator Magnet for Multidimensional Magnetic Particle Imaging", arxiv.org, Jan. 2017) constructed a one-sided coil geometry to generate a field free line for magnetic particle imaging. The assembly consists of two layers of coils, wherein a first pair of coils is arranged in a first layer and is driven with co-rotating currents to thereby obtain a magnetic field gradient above the coils. Based on an elongated shape of the coils and a specific spacing criterion, the magnetic field gradient forms an FFL in a center position with respect to the pair of coils. This FFL may then be displaced along two directions using three coils accommodated in the second layer. Mechanical rotation of the assembly can then allow obtaining a third degree of freedom for the displacement of the FFL and thus 3D scanning of the probe volume.

SUMMARY OF THE INVENTION

Detection systems using FFPs to spatially select sequentially investigated regions suffer from low signal-to-noise ratio and low scanning speed. At the same time, both the three dimensional detection of a presence of magnetic particles based on an FFL as well as a measurement based on rotational drift spectroscopy/imaging rely on the ability to produce a controlled rotation of a magnetic field distribution and currently suffer from control and speed limitations due to mechanically moving parts. Moreover, the known one-sided coil geometries often suffer from strongly asymmetric fields and/or low gradients along the direction going away from the coils.

In view of this state-of-the-art, the object of the invention is to provide a system and method for the one-sided measuring of magnetic particles using time dependent magnetic fields generated by a one-sided coil assembly with an improved control over the spatial distribution of the magnetic field with an electrically rotatable magnetic field distribution.

This object is solved by a system, computer program and method for one-sided measuring a presence of magnetic particles with a one-sided coil assembly according to the independent claims. The dependent claims relate to preferred embodiments.

The invention is in the following described with reference to use in medical imaging and biological research, but may also find applications in different fields benefiting from spatially resolved density information on magnetizable particles, such as the investigation of material composition or workpieces.

If not explicitly mentioned, any gradients, field strengths and field free regions should be considered to relate to magnetic field gradients, magnetic field strengths and magnetic field free regions. Particularly, for the sake of convenience, a magnetic field free line will be referred to as "FFL" or "field free line". Such a field free line defines, along its extension direction, a columnar region with a magnetic field strength smaller than the magnetic saturation field to magnetically saturate the investigated magnetizable particles or magnetizable portions, and is defined within a region having a magnetic field strength above said magnetic saturation field, such as being defined in a region having the shape of a hollow cylinder and having a magnetic field strength above said magnetic saturation field outside of the hollow portion of the cylinder.

It is noted that in real physical systems, a full magnetic saturation can only be achieved approximately. Hence, the magnetic saturation field can be considered to be the field above which the particle shows paramagnetic response to magnetic field changes, i.e. above which the relation between magnetizing field and magnetic field at or close to the particle levels off and is substantially linear. Thus, a non-linear response of the magnetic field to an externally applied magnetizing field can be attributed to the spatial volume defined by the field free line.

In the context of one-sided coil assemblies in real physical systems, said FFL will usually not correspond to a straight line. Rather, the "line" defining the extension of the FFL may be curved or warped. Suitable calculus for simulating an expected location and shape of the FFL is known in the art and can be used to nonetheless derive an image from excitations close to a curved and/or warped FFL. Accordingly, the geometric definitions for the orientations of magnetic fields or FFLs based on a "parallel" or "perpendicular" alignment should be considered as roughly "parallel"/"perpendicular", wherein a relative orientation may deviate from a relative "parallel"/"perpendicular" alignment by up to 30°, in particular by up to 20°, preferably by up to 10°, and/or wherein a relative alignment may be based on a mean or median orientation of an object to account for the deviation from a straight line, and/or may be considered to be defined only in a center of the one-sided coil assemblies used in the systems and methods.

According to a first aspect, the invention relates to a system for one-sided measuring a presence of magnetic particles in a probe volume. The system comprises a one-sided coil assembly and a current controller. The one-sided coil assembly is arranged around a central coil assembly axis for generating a rotating magnetic field distribution. The one-sided coil assembly comprises at least 3, preferably at least 4, circumferentially distributed coil assembly sectors, wherein said coil assembly sectors are arranged circumferentially with respect to said coil assembly axis. The current controller is configured to generate a time varying current in each of said coil assembly sectors, said time varying current comprising a periodic modulation with a rotation frequency. The periodic modulation is phase shifted between adjacent coil assembly sectors to generate a magnetic field rotating in a plane perpendicular to the coil assembly axis, said magnetic field rotating with a rotation frequency associated with a frequency of said periodic modulation. The system is configured for measuring said presence of magnetic particles in said probe volume with said one-sided coil assembly, wherein said probe volume is spaced from said one-sided coil assembly along said coil assembly axis.

The probe volume will in the following be described according to characteristic positions on or close to the coil axis. Nevertheless, the probe volume, which can be scanned by the different embodiments, usually extends beyond said defining characteristic positions and can be reduced as needed by limiting the current amplitudes of the time varying currents or can be partitioned by modulating the currents in a step-wise manner. Hence, the described translation and modulation sequences should be considered illustrative rather than limiting. Accordingly, the term "rotating" should be construed broadly as providing a set of different (discrete) orientations, each rotated at a different angle around the coil assembly axis.

The magnetic particles may be distributed throughout an investigated sample and may be superparamagnetic nanoparticles, such as superparamagnetic iron oxide particles exhibiting a nonlinear magnetization response to externally applied fields below a corresponding saturation field for FFL based detection schemes, or may be ferromagnetic/superparamagnetic nanoparticles exhibiting a large ratio between the magnetic moment of the particle and its volume.

The system may then drive circumferentially arranged coils located in each of the coil assembly sectors with phase shifted time varying currents, such that oppositely arranged coils are driven with counterrotating currents to define a magnetic field which may be aligned parallel to a top surface of the one-sided coil assembly at least close to the coil assembly axis. Using said periodic modulation of the time varying current, a magnitude of the magnetic field component along a given direction may be periodically inverted. In combination with said phase shift of the time varying current between adjacent coil assembly sectors, an electrically controlled effective rotation of the magnetic field distribution around the coil assembly axis can be achieved with the one-sided coil assembly. The resulting magnetic field vector associated with said counterrotating currents in corresponding coils of oppositely arranged coil assembly sectors may then rotate in a plane perpendicular to the coil assembly axis at least in a point on the central coil assembly axis.

In some embodiments, the rotating magnetic field is used to excite a rotation of the magnetic particles for detecting a presence of a magnetic particle based on rotational drift spectroscopy. A magnetic response of said magnetic particles may depend on the rotation frequency and/or the field strength of the rotating magnetic field and may accordingly be attributed to a density of magnetic particles in the probe volume. The magnetic particles may further be functionalized to bind with selected analytes in an investigated sample, wherein a fluid resistance and/or inertia of the magnetic particle may depend on the presence of analytes at its surface. Thus, measuring the response of said magnetic particles in said probe volume to the rotating magnetic field distribution may allow inferring a concentration of analytes in said probe volume.

The response of said magnetic particles may be measured by said system by detecting a current in a dedicated measurement coil, such as a measurement coil whose center is arranged at or close to the coil assembly axis. However, the response of said magnetic particles may equally be obtained by measuring a current in a specific frequency range in at least one coil used for generating said rotating magnetic field distribution, such as by detecting lower frequency components associated with asynchronous rotation of said magnetic particles in said rotating magnetic field or by selecting higher harmonics of said rotation frequency using a high-pass filter, wherein said higher harmonics of said rotation frequency may be associated with a nonlinear response of the magnetic nanoparticles. Frequency analysis of the obtained magnetization response of the magnetic particles may then be used to infer a presence and/or density of said magnetic particles in said probe volume.

In preferred embodiments, the one-sided coil assembly comprises a number of N circumferentially distributed coil assembly sectors, and the periodic modulation is phase shifted between adjacent coil assembly sectors by an Nth part of a rotation period which is proportional to the inverse of said rotation frequency f, in particular by $2\pi/f*N$.

Preferably, the number N of circumferentially distributed coil assembly sectors is three or four, wherein a number of three circumferentially distributed coil assembly sectors may allow providing a dense arrangement of hexagonally arranged one-sided coil assemblies, while a number of four circumferentially distributed coil assembly sectors may provide a more homogeneous magnetic field distribution while limiting the number of independently controlled current lines to be controlled by the current controller.

By phase shifting the periodic modulation between adjacent coil assembly sectors by equal parts of $2\pi$, a uniform rotation of the magnetic field distribution may be obtained.

In preferred embodiments, said circumferentially distributed coil assembly sectors are each arranged in a circular sector, in particular arranged in an annular sector, around the coil assembly axis, wherein said circular sectors are uniformly distributed around said coil assembly axis.

Each of said circular or annular sectors may span an equal angular range around the coil assembly axis, wherein said angular range is in particular the Nth part of $2\pi$ or deviates from the Nth part of $2\pi$ by less than 20%, preferably by less than 10%, with N being the number of circumferentially arranged coil assembly sectors, such that each of the coil assembly sectors is arranged in a separate angular range around the coil assembly axis. The at least 3 or at least 4 coil assembly sectors may then together form the shape of an annulus around the coil assembly axis.

In some embodiments, a measurement coil is arranged in a center of the one-sided coil assembly, and said circumferentially distributed coil assembly sectors are annular sectors surrounding said measurement coil.

In preferred embodiments, each of the circumferentially distributed coil assembly sectors comprises an inner coil and an outer coil, a center of said inner coil being arranged closer to the coil assembly axis than a center of the outer coil.

For an application in rotational drift spectroscopy, said inner coil and said outer coil may be driven with co-rotating currents to increase a homogeneity of the magnetic field distribution as compared to driving a single coil of each coil assembly sector with said time varying current. A current amplitude in said inner and outer coils may generally be different.

In some embodiments, one of the inner coil and the outer coil is driven with said time varying current to provide a rotating magnetic field, while the other of said inner coil and said outer coil may be driven with a second current to induce a magnetic field gradient in said probe volume for spatially selecting magnetic particles, wherein said second current may induce a magnetic field gradient aligned perpendicular to the coil assembly axis at least on the coil assembly axis. Said gradient may introduce a phase or frequency shift in response of said magnetic particles to create a correspondence between a property of the measurement signal and the spatial origin of the magnetic particle response. Further details regarding the encoding of the spatial origin using gradients and the corresponding detection schemes can be found in DE 102010013900 A1, hereby incorporated herein by reference.

In preferred embodiments, a winding of said inner coil and/or said outer coil comprises a pair of radially extending wires, an inner circumferentially extending wire and an outer circumferentially extending wire.

Said radially extending wires may extend along a line perpendicular to the coil assembly axis and may connect endpoints of said inner and outer circumferentially extending wires. Said inner and outer circumferentially extending wires may each correspond to circle arcs or straight connections. An arc shape of said inner and/or outer circumferentially extending wires may improve a rotational symmetry of said magnetic field distribution, while a deviation from said arc shape may improve a stability of coil windings of said inner coil and/or outer coil, and/or may facilitate manufacture of the one-sided coil assembly.

In preferred embodiments, the inner coil and the outer coil do not overlap when viewed along the coil assembly axis, wherein the inner coil and the outer coil in particular comprise windings extending perpendicular to the coil assembly axis, or wherein the inner coil and the outer coil in particular each consist of a single winding arranged in a plane perpendicular to the coil assembly axis.

Non-overlapping inner and outer coils may simplify a manufacturing of the one-sided coil assembly and may in particular enable concurrent manufacturing of the inner coil and the outer coil using lithography or layering of conductive traces for providing miniaturized one-sided coil assemblies. In addition, physically separating the inner coil and the outer coil may assist a generation of a field free space in said probe volume.

In preferred embodiments, the magnetic field distribution comprises a field free line (FFL), and said current controller is configured to drive the inner coil and the outer coil of each of said circumferentially distributed coil assembly sectors with counterrotating currents to generate a first magnetic field aligned perpendicular to the coil assembly axis at least in a first point on the coil assembly axis, wherein the first magnetic field has a first orientation and is associated with the inner coils, and a second magnetic field aligned perpendicular to the coil assembly axis at least in a second point on the coil assembly axis, wherein the second magnetic field has a second orientation, which is inverse to said first orientation, and is associated with the outer coils. Said first point and said second point are spaced along said coil assembly axis, and said field free line is arranged between said first point and said second point.

Thus, said first magnetic field associated with the inner coils and said second magnetic field associated with the outer coils may generate a magnetic field gradient along said coil assembly axis, wherein a magnetic field along said coil assembly axis may switch orientation between said first point and said second point, to define the FFL. Accordingly, the FFL may extend along a direction perpendicular to the coil assembly axis, at least close to said coil assembly axis. The FFL may be formed midways between currently active oppositely arranged coil assembly sectors (i.e. associated with the currently largest current amplitude when driven with said time varying current), and an extension direction of the FFL may hence be aligned perpendicular to a line connecting the currently active oppositely arranged coil assembly sectors. As compared to prior art coil assemblies, the use of oppositely arranged pairs of inner and outer coils allows defining said first and second points on the coil assembly axis associated with respective pairs of said inner and outer coils enabling dynamic control over a magnetic field gradient along the coil assembly axis. Therefore, driving the inner coil and the outer coil with counterrotating currents may allow limiting a spatial extension of the FFL along said coil assembly axis to advantageously affect a spatial resolution of an FFL based measurement sequence along the coil assembly axis.

Driving said circumferentially distributed coil assembly sectors with said time varying current induces a periodic change of the currently active oppositely arranged coil assembly sectors, effectively rotating the FFL around the coil assembly axis.

In other words, the inner coil and the outer coil of each coil assembly sector may be driven with time varying currents comprising said periodic modulation, wherein a current direction of said time varying current in the inner coil and the outer coil of the same coil assembly sector is inverse, and wherein the time varying currents in the inner coil and the outer coil of the same coil assembly sector are attributed the same phase shift, to induce a rotating field free line in said probe volume.

In preferred embodiments, the current controller is further configured to generate a second time varying current in each of said coil assembly sectors, said second time varying current comprising the periodic modulation with the rotation frequency and being phase shifted between adjacent coil assembly sectors and further comprising a second periodic modulation with a height modulation frequency, to generate a co-rotating field component at least in a third point between said first point and said second point rotating with said rotating frequency, a field strength of said co-rotating field component being modulated with said height modulation frequency to shift said rotating field free line along the coil assembly axis.

For example, the second time varying current may comprise a first sinusoidal modulation with the rotation frequency and phase shifted between adjacent coil assembly sectors, and a second sinusoidal modulation with the height modulation frequency, wherein the first sinusoidal modulation in the second sinusoidal modulation are multiplied with each other to obtain a periodic modulation of the second time varying current.

The second time varying current may be applied to at least one of the inner coil and the outer coil in addition to the (first) time varying current comprising the periodic modulation with the rotation frequency, such as to drive the inner and outer coils of each coil assembly sector with corotating and counterrotating current components, the corotating current components inducing a magnetic field component having a substantially uniform orientation between said first and second points, such that said FFL may be defined and shifted along said coil assembly axis with said counterrotating and corotating current components, respectively.

In preferred embodiments, the one-sided coil assembly comprises a height modulation coil in each of said circumferentially distributed coil assembly sectors, a center of said height modulation coil being farther from the coil assembly axis than the center of said inner coil and being closer to the coil assembly axis than the center of said outer coil, wherein a winding of the height modulation coil in particular encloses a winding of the inner coil and the outer coil when viewed along said coil assembly axis. Said second time varying current may then be applied to said height modulation coil.

Providing a dedicated height modulation coil in each of said circumferentially distributed coil assembly sectors, wherein said winding of the inner coil and the outer coil in particular encloses the inner coil and the outer coil when viewed along said coil assembly axis, may allow generating said co-rotating field component with a higher homogeneity along the coil assembly axis as compared to driving the inner and outer coils with the second time varying current, and may allow simplifying a corresponding driving circuit of the current controller.

In preferred embodiments, the current controller is further configured to generate a third time varying current in said one-sided coil assembly comprising a periodic modulation with a radial translation frequency to generate a magnetic field component along said coil assembly axis in said probe volume to displace the field free line along a radial displacement direction with respect to the coil assembly axis, said radial displacement direction being perpendicular to a current extension direction of the field free line, wherein the one-sided coil assembly in particular further comprises a radial displacement coil, a center of the radial displacement coil being arranged at or close to the coil assembly axis, wherein a winding of the radial displacement coil preferably encloses the inner coils and/or the outer coils of a plurality, and preferably all, of said circumferentially distributed coil assembly sectors when viewed along said coil assembly axis.

Thus, using the first, second and third time varying currents, the FFL may be rotated and displaced along two directions perpendicular to a current extension direction of the FFL, respectively, thereby enabling a measurement of magnetic particles in said probe volume spatially resolved along three dimensions.

In principle, the third time varying current could also be applied to the inner coil and/or the outer coil of a plurality, and in particular all, of the circumferentially distributed coil assembly sectors in phase, to generate said magnetic field component along the coil assembly axis. However, providing a dedicated radial displacement coil may enhance a field homogeneity of said magnetic field component perpendicular to the coil assembly axis and therefore a linearity of a radial displacement of the FFL in the probe volume. Further, providing a dedicated radial displacement coil may simplify driving circuits and may allow defining a sharp radial displacement frequency. In some embodiments, the radial displacement coil is also used to measure a response of the magnetic particles in the probe volume.

While the properties of the height modulation coil and the radial displacement coil have been highlighted with an example of an FFL, said coils may equally be employed advantageously in applications relating to rotational drift spectroscopy/imaging, wherein the height modulation coil in each of said coil assembly sectors may be driven with a current proportional to the time varying current to smooth a magnetic field homogeneity of the rotating magnetic field in the probe volume. The radial displacement coil may further be used as a measurement coil, as an offset coil driven with a DC current, or as a pulsing coil for aligning magnetic nanoparticles along the coil assembly axis e.g. with a Delta pulse applied to the radial displacement coil.

In preferred embodiments, a top surface of the one-sided coil assembly facing the probe volume is flat or concave, wherein an angle between radially outward faces of the top surface and the coil assembly axis is less than 45°, in particular less than 30°, preferably less than 15°.

Thus, the side of the one-sided coil assembly facing the probe volume can comprise a concave portion, which may improve a field homogeneity as compared to a flat top surface while remaining substantially one-sided for the purposes of not restricting an extension of an investigated sample along the coil assembly axis.

In preferred embodiments, the system further comprises a plurality of one-sided coil assemblies arranged in rows and/or columns to define rows and/or columns of a sensor array for measuring a presence of magnetic particles in a plurality of probe volumes of associated one-sided coil assemblies above said plurality of one-sided coil assemblies.

Therefore, the system may comprise a lattice of regularly spaced one-sided coil assemblies, wherein each of said one-sided coil assemblies is configured for detecting a presence of magnetic particles in a probe volume associated with said one-sided coil assembly. In other words, each coil assembly may be considered as a pixel of a detector for the presence of magnetic particles. For an application in rotational drift spectroscopy, each of said coil assemblies in the lattice of one-sided coil assemblies may be driven with the (first) time varying current. In some embodiments, different current amplitudes or modulation frequencies may be provided in each of the one-sided coil assemblies, such as to individualize a response of magnetic particles in a probe volume associated with a respective one-sided coil assembly. In some embodiments, each coil assembly comprises a measurement coil to measure a local response of magnetic particles close to the coil assembly.

In preferred embodiments, the one-sided coil assembly is microscopic and has a radial extension perpendicular to the coil assembly axis of less than 10 mm, in particular less than 1 mm, preferably less than 100 micrometer, most preferably on the order of a size of a cellular organism of one cell or less than 100 cells, or smaller than a size of a cell.

A microscopic coil assembly may be manufactured using lithography techniques commonly used in microelectronics to define current traces on a substrate. When the radial extension of the coil assembly is on the order of a size of a cellular organism or smaller than a size of a cell, the one-sided coil assembly can be used to resolve a spatial distribution of the magnetic particles within said cellular organism or within said cell, in particular using a plurality of one-sided coil assemblies arranged in a lattice. Based on the one-sided geometry of the one-sided coil assembly, a measurement with said microscopic coil can then be advantageously combined with optical measurements e.g. using a microscope, allowing concurrent optical and magnetic measurement of cellular organisms with cellular or subcellular resolution of a location of magnetic particles in said cellular organism.

In a second aspect, the invention relates to a method for one-sided measuring a presence of magnetic particles in a probe volume with a one-sided coil assembly arranged around a central coil assembly axis, wherein said probe volume is spaced from of the one-sided coil assembly along said coil assembly axis. The one-sided coil assembly comprises at least 3, preferably at least 4, circumferentially distributed coil assembly sectors, wherein said coil assembly sectors are arranged circumferentially with respect to said coil assembly axis. The method comprises generating a rotating magnetic field distribution by generating a time varying current in each of said coil assembly sectors, said time varying current comprising a periodic modulation, wherein said periodic modulation is phase shifted between adjacent coil assembly sectors to generate a magnetic field rotating in a plane perpendicular to the coil assembly axis, said magnetic field rotating with a rotation frequency associated with a frequency of said periodic modulation.

In preferred embodiments, the method according to the second aspect further comprises providing any one of the systems of the first aspect or implements any one of the functionalities of the systems according to the first aspect, such as by providing and/or varying currents in said systems according to the first aspect.

In preferred embodiments, the magnetic field distribution comprises a field free line, and the method comprises driving an inner coil and an outer coil of each of said circumferentially distributed coil assembly sectors with counterrotating currents for generating a first magnetic field aligned perpendicular to the coil assembly axis at least in a first point on the coil assembly axis, wherein the first magnetic field has a first orientation and is associated with the inner coils, and a second magnetic field aligned perpendicular to the coil assembly axis at least in a second point on the coil assembly axis, wherein the second magnetic field has a second orientation, which is inverse to said first orientation, and is associated with the outer coils. The first point and the second point are spaced along said coil assembly axis, and the field free line is arranged between said first point and said second point.

In preferred embodiments, the method further comprises generating a second time varying current in each of said coil assembly sectors, said second time varying current comprising the periodic modulation with the rotation frequency and being phase shifted between adjacent coil assembly sectors and further comprising a second periodic modulation with a height modulation frequency, for generating a co-rotating field component at least in a third point between said first point and said second point rotating with said rotating frequency, a field strength of said co-rotating field component being modulated with said height modulation frequency to shift said rotating field free line along the coil assembly axis.

In some embodiments, the one-sided coil assembly comprises a height modulation coil in each of said circumferentially distributed coil assembly sectors, a center of said height modulation coil being farther from the coil assembly axis than a center of said inner coil and being closer to the coil assembly axis than a center of said outer coil, wherein a winding of the height modulation coil in particular encloses a winding of the inner coil and the outer coil when viewed along said coil assembly axis, and the method comprises applying said second time varying current to said height modulation coil.

In preferred embodiments, the method further comprises generating a third time varying current in said one-sided coil assembly comprising a periodic modulation with a radial translation frequency for generating a magnetic field component along said coil assembly axis in said probe volume for displacing the field free line along a radial displacement direction with respect to the coil assembly axis. The radial displacement direction is perpendicular to a current extension direction of the field free line.

In some embodiments, the one-sided coil assembly further comprises a radial displacement coil, a center of the radial displacement coil being arranged at or close to the coil assembly axis, wherein a winding of the radial displacement coil preferably encloses the inner coils and/or the outer coils of a plurality, and preferably all, of said circumferentially distributed coil assembly sectors when viewed along said coil assembly axis. The method then comprises applying said third time varying current to said radial displacement coil.

In preferred embodiments, the method further comprises providing a plurality of one-sided coil assemblies arranged in rows and/or columns to define rows and/or columns of a sensor array for measuring a presence of magnetic particles in a plurality of probe volumes of associated one-sided coil assemblies above said plurality of one-sided coil assemblies.

In preferred embodiments, the method further comprises driving each of said one-sided coil assemblies with said time varying current.

In some embodiments, the method comprises driving each of said one-sided coil assemblies with said time varying current, wherein the current amplitudes in different one-sided coil assemblies are different and/or wherein said rotation frequency assumes different values for different one-sided coil in said sensor array.

In some embodiments, the method comprises driving each of said one-sided coil assemblies with a time varying current, wherein the current amplitudes in different one-sided coil assemblies are different.

In some embodiments, the method comprises measuring a presence of magnetic particles in a plurality of probe volumes associated with corresponding one-sided coil assemblies of the sensor array using a measurement coil arranged in each one-sided coil assembly.

In a third aspect, the invention relates to a computer program or computer program product comprising machine readable instructions, which when the computer program is executed by a processing unit cause the processing unit to control a system according to any embodiment of the system according to the first aspect and/or to implement a method according to any one of the embodiments of the second aspect.

The machine readable instructions of the computer program or computer program product may be stored on a non-transitory machine-readable storage medium to be accessed by the processing unit.

DETAILED DESCRIPTION OF EMBODIMENTS

The features and numerous advantages of the method, computer program and system according to the present invention will best be understood from a detailed description of preferred embodiments with reference to the accompanying drawings, in which:

FIG. 1 schematically shows an example of a system for one-sided measuring a presence of magnetic particles;

FIG. 2 illustrates a schematic one-sided coil assembly according to an example;

FIG. 3A schematically illustrates a side view of magnetic field directions generated by oppositely arranged coil assembly sectors in an exemplary current configuration;

FIG. 3B schematically illustrates a perspective view of magnetic field directions generated by oppositely arranged coil assembly sectors in an exemplary current configuration;

FIG. 4A, 4B illustrate two perspective views of oppositely arranged coil assembly sectors superposed with a schematic representation of a field free line generated in an exemplary current configuration by the oppositely arranged coil assembly sectors according to an example;

FIG. 4C, 4D illustrate two schematic top views of a one-sided coil assembly in two different current configurations corresponding to two different orientations of the field free line generated by the one-sided coil assembly according to an example;

Figure 6A:
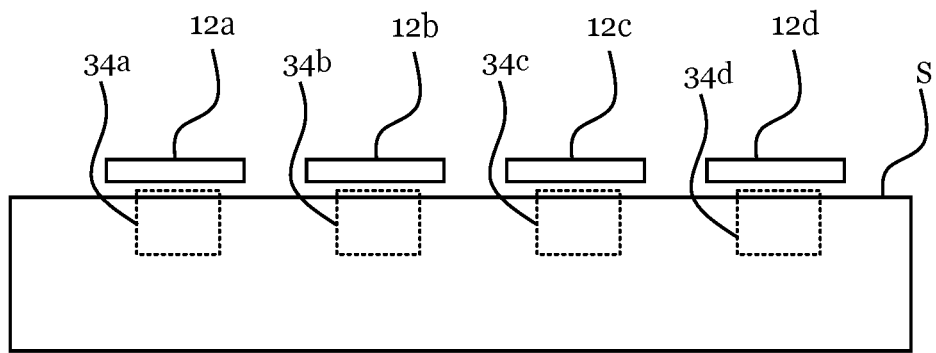
Figure 6B:
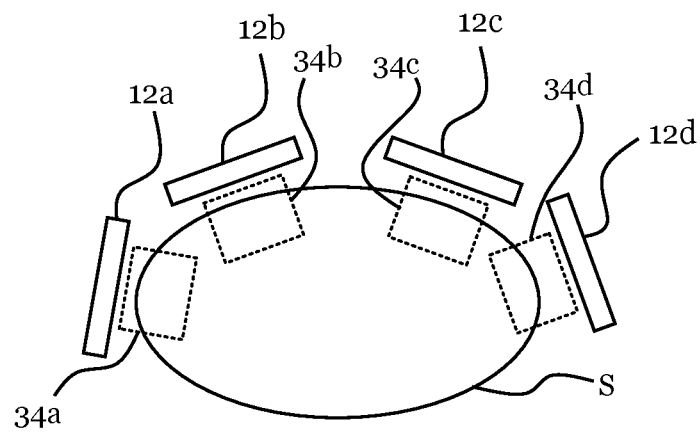
Figure 6C:
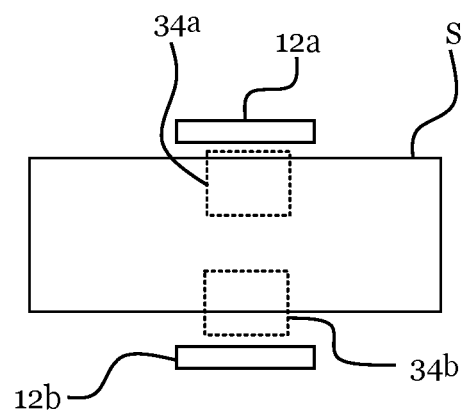
Figure 7A:
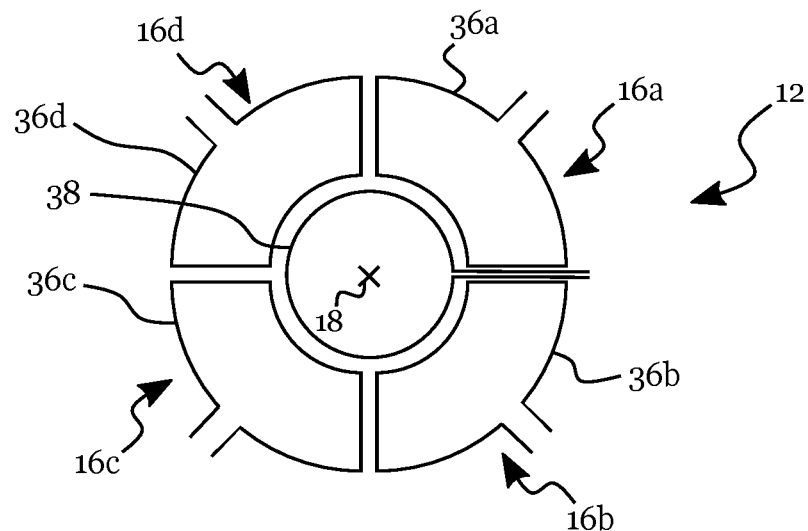
Figure 7B:
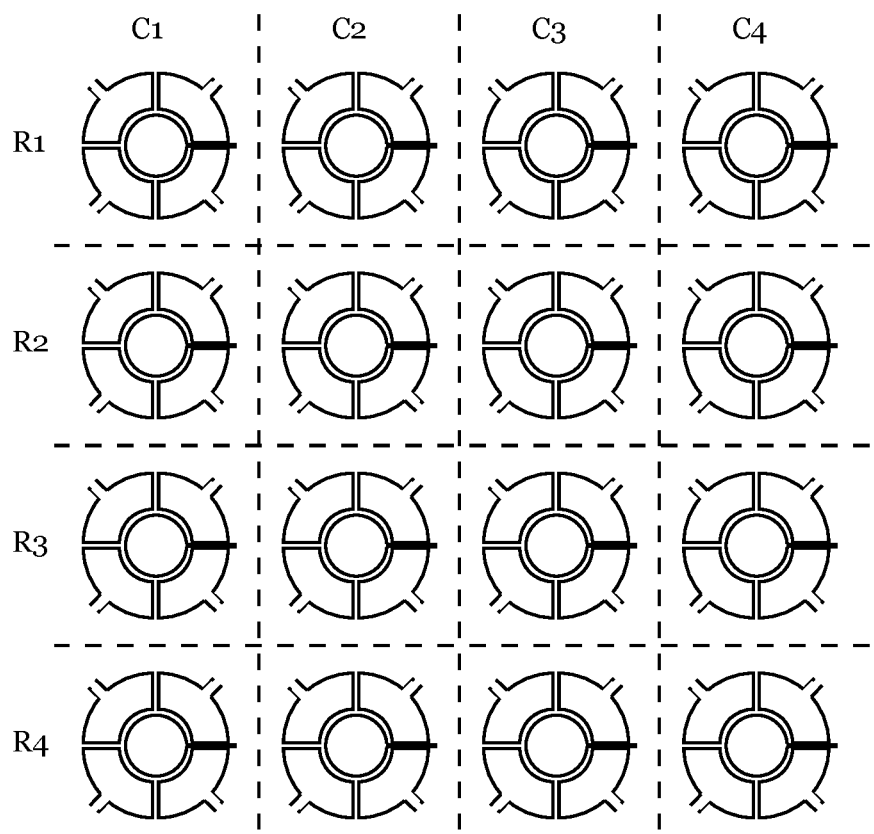

FIG. 6A-C illustrates three examples of a concurrent measurement of a presence of magnetic particles in a sample with a plurality of one-sided coil assemblies;

FIG. 7A illustrates a planar coil geometry comprising four circumferentially arranged planar coils and a central measurement coil according to an example; and FIG. 7B illustrates a sensor array of one-sided coil assemblies arranged in rows and columns according to an example.

Figure 1A:
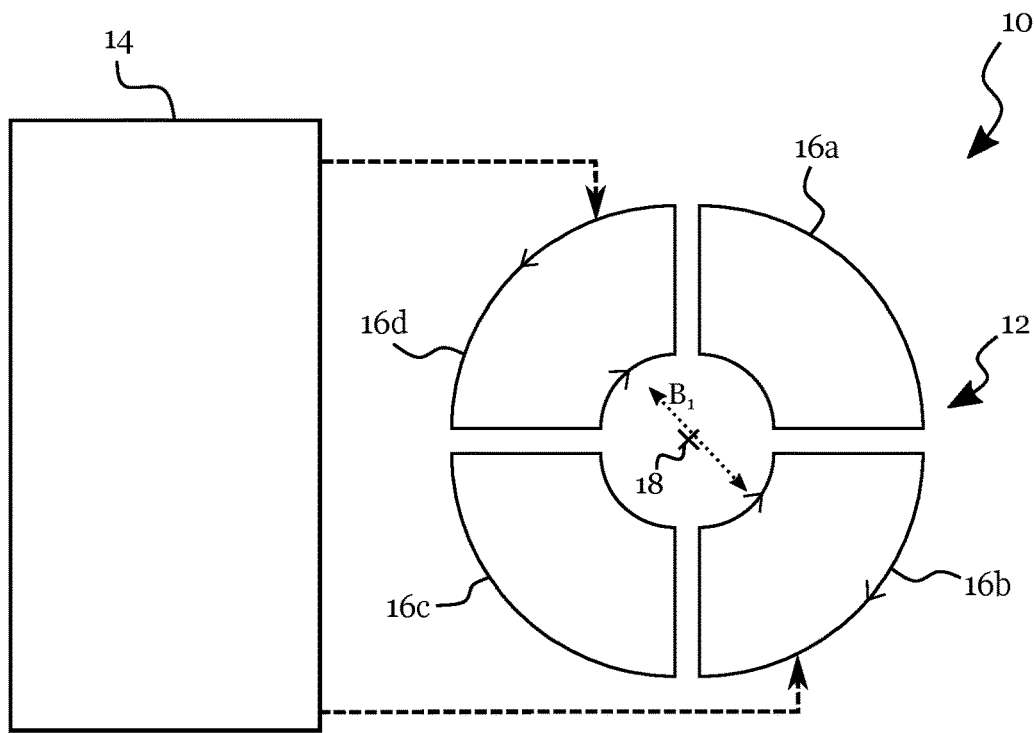
Figure 1B:
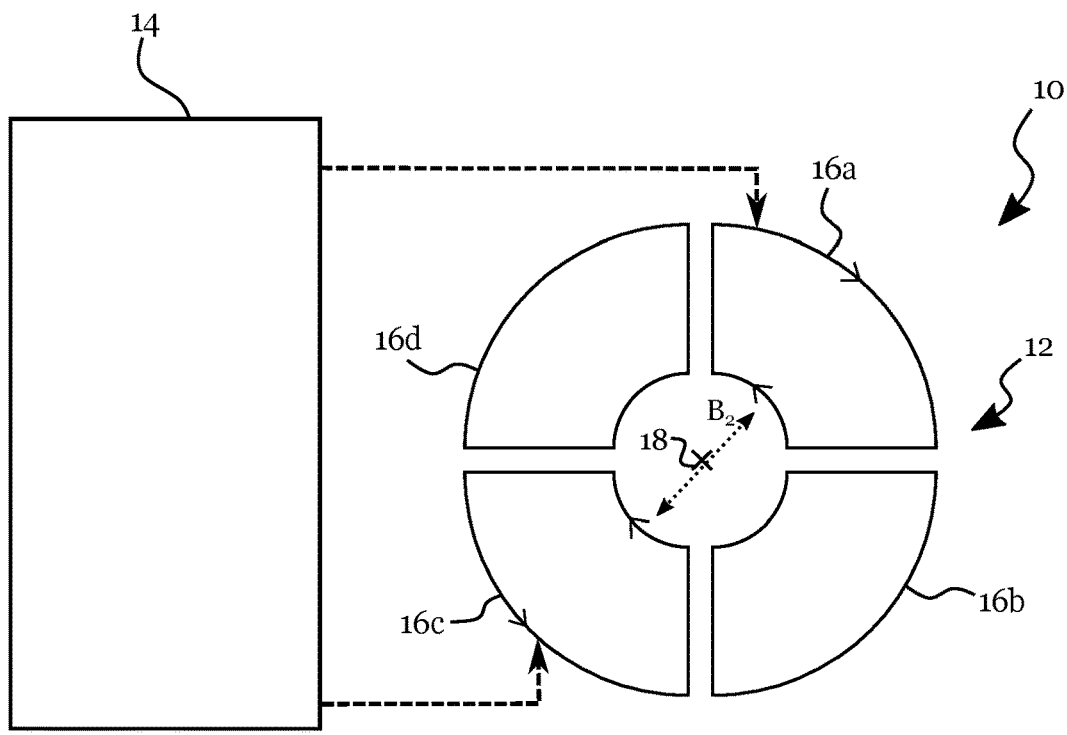

FIGS. 1A and 1B illustrate two configurations of a system 10 for one-sided measuring a presence of magnetic particles in a probe volume according to an example. The system 10 comprises a one-sided coil assembly 12 and a current controller 14. The one-sided coil assembly 12 is illustrated according to a top view onto said one-sided coil assembly 12 and comprises four coil assembly sectors 16a-d circumferentially distributed around a coil assembly axis 18 (extending perpendicular to the plane of projection), wherein each coil assembly sector 16a-d is illustrated with a single coil having a shape of an annular sector spanning an angular range of 900 around the coil assembly axis 18.

The current controller 14 can be configured to drive said coil assembly sectors 16a-d with a time varying current for generating a magnetic field distribution $B_1/B_2$ schematically illustrated with a corresponding characteristic axis (dashed double-headed arrow). In FIG. 1A, the current controller 14 drives the oppositely arranged coils in the coil assembly sectors 16b and 16d with counterrotating currents (direction being indicated with arrowheads on the respective coils), inducing a magnetic field component close to the coil assembly axis 18 substantially aligned along the depicted characteristic axis of the magnetic field distribution $B_1$ and spaced from the one-sided coil assembly 12 along the coil assembly axis 18.

FIG. 1B illustrates another configuration of the system 10, wherein the current controller 14 is configured to drive the coil assembly sectors 16a, 16c with counterrotating currents (indicated with arrowheads on the respective coils) to generate a magnetic field distribution $B_2$, which is rotated with respect to the magnetic field distribution $B_1$ illustrated in FIG. 1A.

By periodically switching between the configuration illustrated in FIG. 1A and the configuration illustrated in FIG. 1B, the orientation of the magnetic field distribution $B_1/B_2$ can be periodically varied. In particular, driving each of the coil assembly sectors 16a-d with a time varying current comprising a periodic modulation, such as a sinusoidal modulation, wherein said time varying current is phase shifted between adjacent coil assembly sectors 16a-d by a quarter of a period of the frequency of the periodic modulation, i.e. $\pi/2$, a largely uniform rotation of the magnetic field distribution $B_1/B_2$ around the coil assembly axis 18 may be obtained.

In the depicted example of a system 10, said rotating magnetic field distribution $B_1/B_2$ may correspond to a magnetic field rotating in a plane perpendicular to the coil assembly axis 18 at least in a probe volume spaced along the coil assembly axis 18 from the one-sided coil assembly 12. Magnetic particles in an at least partially fluid sample located in said probe volume, in particular ferromagnetic or superparamagnetic nanoparticles with diameters between 20 and 200 nm, may accordingly align their magnetization with said external rotating magnetic field and may thus give rise to a magnetization response to said magnetic field distribution $B_1/B_2$. However, depending on a magnetic field strength and a rotation frequency associated with said rotating magnetic field, magnetic particles may exhibit a critical frequency above which said particles exhibit a rotational drift, wherein the magnetization of said magnetic particles no longer strictly follows the externally applied rotating magnetic field but lags behind giving rise to off-frequency terms or phase shifts between the externally applied field and the magnetization response. Thus, by measuring the magnetization response, for example by measuring a current in a measurement coil (not shown), the presence of magnetic particles in a probe volume may be measured by the system 10.

Figure 2:
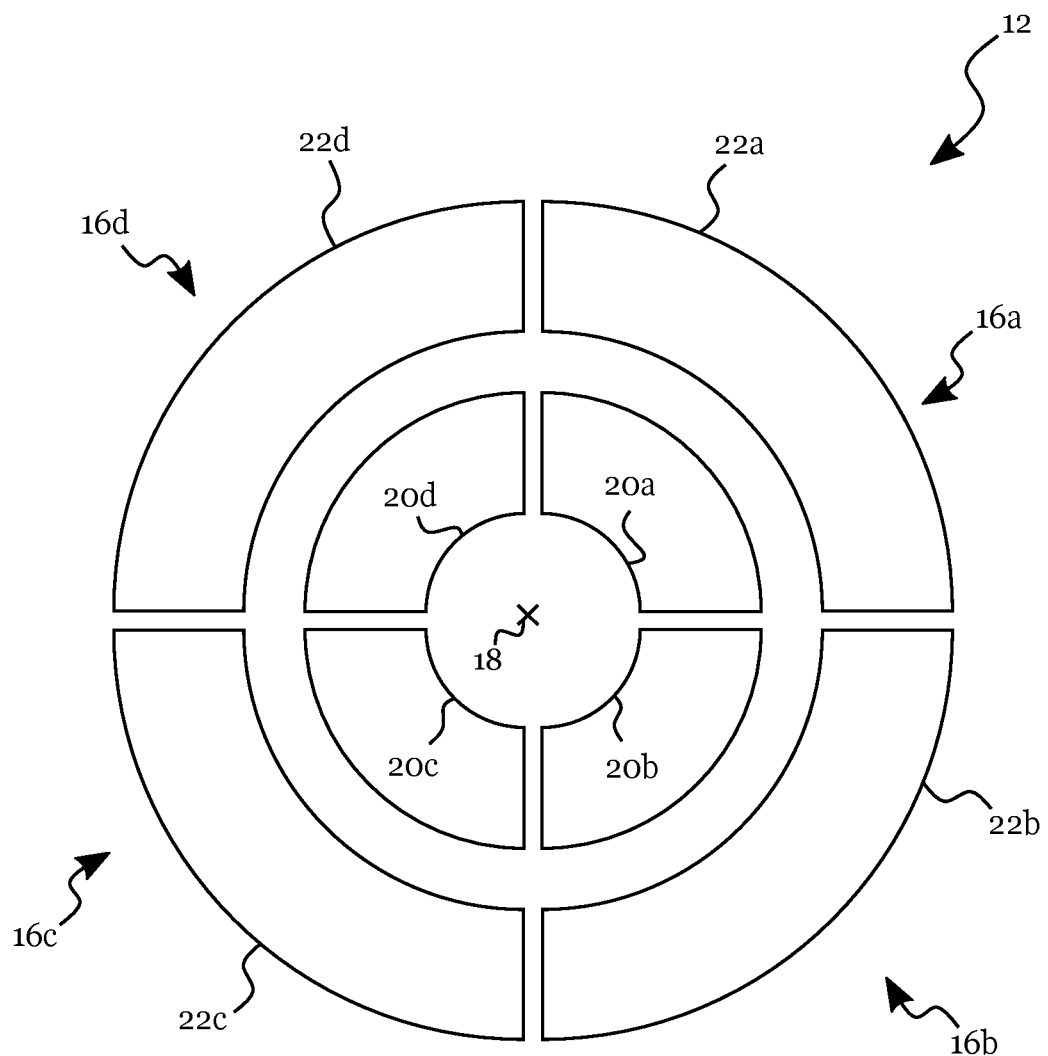

FIG. 2 illustrates a schematic top view of a one-sided coil assembly 12 for measuring a presence of magnetic particles in a probe volume according to an example. The one-sided coil assembly 12 comprises four circumferentially distributed coil assembly sectors 16*a-d* arranged around a common coil assembly axis 18 (extending perpendicular to the plane of projection). Each of the coil assembly sectors 16*a-d* comprises an inner coil 20*a-d* and an outer coil 22*a-d*.

In the illustrated example, the inner coils 20*a-d* and the outer coils 22*a-d* each have a shape of an annular sector spanning the same angular range around the coil assembly axis 18, wherein a center of the inner coils 20*a-d* is closer to the coil assembly axis 18 than a center of the outer coils 22*a-d*, and wherein the inner coils 20*a-d* and the outer coils 22*a-d* do not overlap when viewed along the coil assembly axis 18 but are spaced apart in a direction perpendicular to the coil assembly axis 18.

The one-sided coil assembly 12 of FIG. 2 may be used for a one-sided generation of a field free line in a probe volume spaced from the one-sided coil assembly 12 along the coil assembly axis 18 by concurrently driving the inner and outer coils with time varying currents.

Figure 3A:
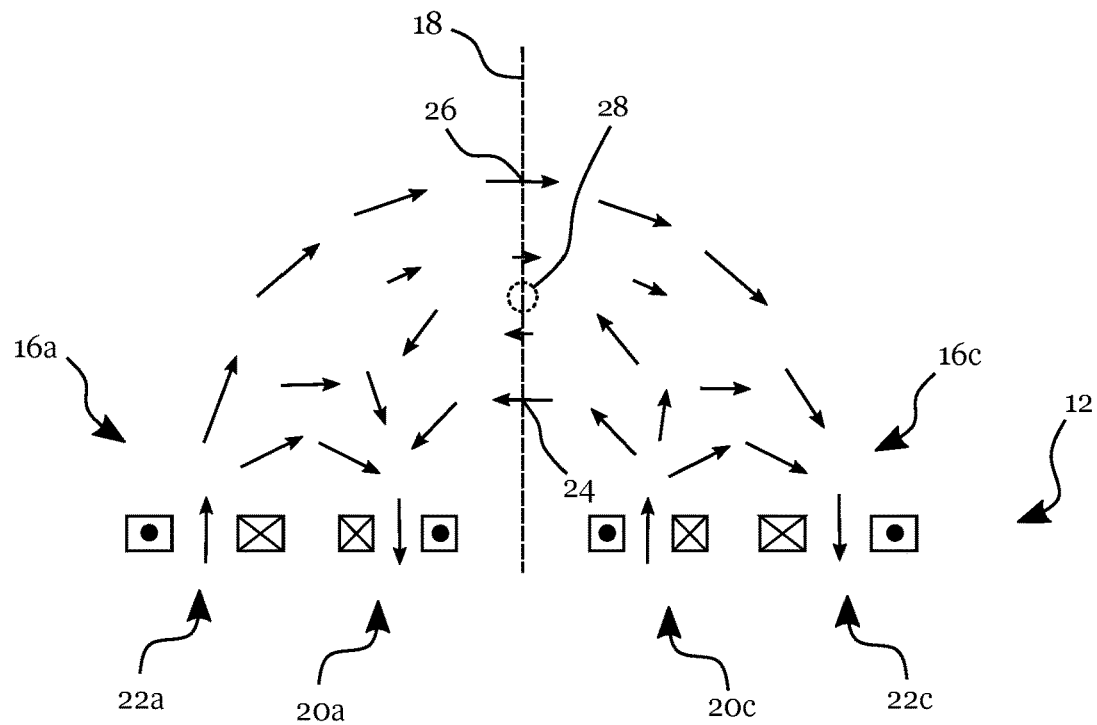

FIG. 3A illustrates a schematic side view of a one-sided coil assembly 12 in a selected current configuration superposed with schematically depicted associated magnetic field lines according to an example. The directions of the currents schematically illustrated in FIG. 3A is illustrated with corresponding symbols inside of the current lines extending perpendicular to the plane of projection, wherein a dot indicates a current coming out of the plane of projection, and wherein a cross indicates a current going into the plane of projection. The magnetic field is illustrated schematically with straight black arrows in different positions close to the coil assembly axis 18, with selected short arrows indicating a lower field strength.

The illustrated one-sided coil assembly 12 of FIG. 3A, which may be similar to the one-sided coil assembly 12 illustrated in FIG. 2, comprises oppositely arranged coil assembly sectors 16*a*, 16*c*, arranged oppositely with respect to a central coil assembly axis 18, wherein each of the coil assembly sectors 16*a*, 16*c* comprises an inner coil 20*a*, 20*c* and an outer coil 22*a*, 22*c*.

In the illustrated configuration of FIG. 3A, the outer coil 22*a* of the coil assembly sector 16*a* is driven with a current running counterclockwise (as viewed along the coil assembly axis 18 from the top), whereas the inner coil 20*a* of the same coil assembly sector 16*a* is driven with a current running clockwise. For the other, oppositely arranged, coil assembly sector 16*c*, the current configuration is inverse, such that the outer coil 22*c* is driven with a current running clockwise, whereas the inner coil 20*c* is driven with a current running counterclockwise.

The resulting magnetic field distribution (illustrated only above the one-sided coil assembly 12) exhibits a first magnetic field connecting the respective inner coils 20*a*, 20*c* of the oppositely arranged coil assembly sectors 16*a*, 16*c*, and a second magnetic field connecting the respective outer coils 22*a*, 22*c* of the oppositely arranged coil assembly sectors 16*a*, 16*c*. Said first magnetic field is oriented perpendicular to the coil assembly axis 18 in a first point 24 on the coil assembly axis 18, wherein a magnetic field direction in said first point is oriented from right to left. The second magnetic field is oriented inverse to the first magnetic field in a second point 26 on the coil assembly axis 18, wherein the second point 26 is spaced farther from the one-sided coil assembly 12 than the first point 24.

However, at a third point 26 on the coil assembly axis 18, the magnetic fields generated by the one-sided coil assembly 12 cancel, such as to form a field free line 28 (FFL) extending perpendicular to the plane of projection.

Figure 3B:
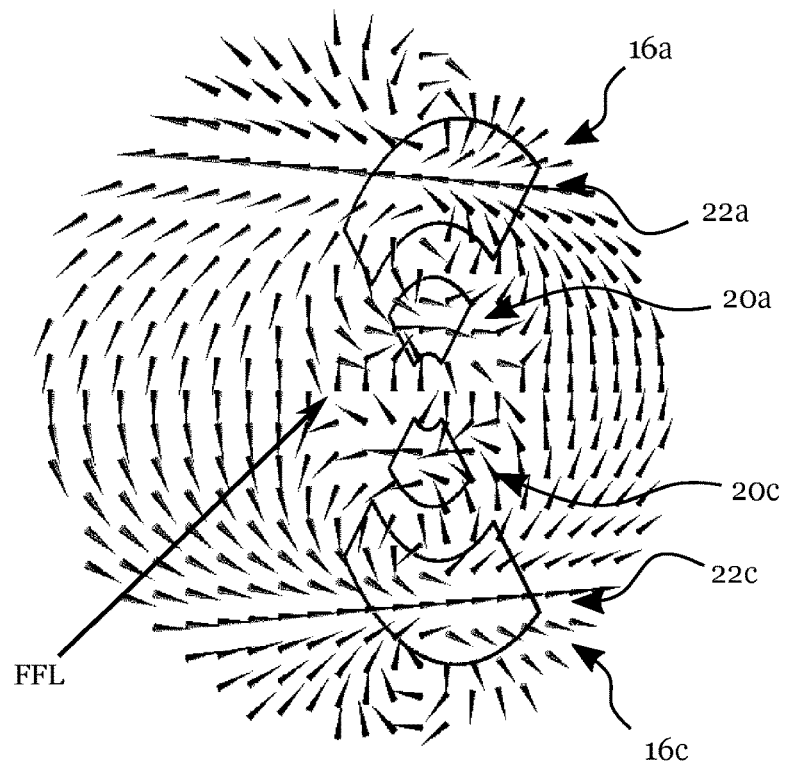

FIG. 3B illustrates a schematic perspective view of oppositely arranged coil assembly sectors 16*a*, 16*c* of a one-sided coil assembly 12 according to an example, such as the one-sided coil assembly 12 of FIG. 2 and FIG. 3A. In addition, a simulation of the magnetic field in a plane perpendicular to the one-sided coil assembly 12 is superposed with the coil geometry, wherein the superposed simulation illustrates the direction of the magnetic field (illustrated with triangular arrows) generated by the oppositely range coil assembly sectors 16*a*, 16*c* when driven as in the example of FIG. 3A. A straight black arrow indicates a region wherein the magnetic fields generated by the coils 20*a*-22*c* of the one-sided coil assembly 12 cancel and form a field free region associated with an FFL.

FIGS. 4A and 4B illustrate two perspective views of a one-sided coil assembly 12 and of an illustration of a corresponding field free line 28 generated by said one-sided coil assembly 12 according to an example. The inner coils 20*a*, 20*c* and the outer coils 22*a*, 22*c* of the oppositely arranged coil assembly sectors 16*a*, 16*c* are driven as schematically illustrated in FIG. 3A to generate said field free line 28. The spatial region illustrated as the field free line 28 defines a columnar region outside of which a magnetic field strength generated by the one-sided coil assembly 12 is above a saturation field for exemplary superparamagnetic particles, such as iron oxide particles with a diameter of 10 to 40 nm.

Said field free line 28 is spaced from the one-sided coil assembly 12 along said coil assembly axis 18 and roughly forms a half torus perpendicular to the coil assembly axis 18 in the center of the one-sided coil assembly 12 and may be arranged between the outer periphery of the one-sided coil assembly 12 and the centers of the inner coils 20*a*, 20*c*. In the illustrated example, an extension direction of said field free line 28 is perpendicular to the coil assembly axis 18 at least in the center of the one-sided coil assembly and is further perpendicular to a connecting line connecting the oppositely arranged coil assembly sectors 16a, 16c.

By driving the inner coils 20a, 20c and the outer coils 22a, 22c with time varying currents comprising a periodic modulation, the magnetic field distribution giving rise to said field free line 28 may be periodically built up/taken down between oppositely arranged coil assembly sectors 16a, 16c or 16b, 16d to change an orientation of the field free line 28 in said probe volume.

For example, a driving sequence may comprise eight time varying currents for the inner coils 20a-d and outer coils 22a-d of the circumferentially distributed coil assembly sectors 16a-d, wherein the driving currents $I_{S1-S4,inner}$ of the inner coils 20a-d of different coil assembly sectors S1-S4 (corresponding to the coil assembly sectors 16a-d illustrated in the Figures) may comprise a sinusoidal modulation associated with a rotation frequency $f_1$ and a modulation amplitude $A_1$ according to:

$$I_{S1,inner} = A_1 * \sin(2\pi f_1 * t);$$

$$I_{S2,inner} = A_1 * \sin(2\pi f_1 * t + \pi/2);$$

$$I_{S3,inner} = A_1 * \sin(2\pi f_1 * t + \pi);$$

$$I_{S4,inner} = A_1 * \sin(2\pi f_1 * t + 3\pi/2);$$

and wherein the outer coils 22a-d of the respective sectors S1-S4 are equally driven with time varying currents $I_{S1-S4,outer}$ comprising a sinusoidal modulation associated with the rotation frequency $f_1$ and a modulation amplitude $A_2$:

$$I_{S1,outer} = A_2 * \sin(2\pi f_1 * t + \pi);$$

$$I_{S2,outer} = A_2 * \sin(2\pi f_1 * t + 3\pi/2);$$

$$I_{S3,outer} = A_2 * \sin(2\pi f_1 * t);$$

$$I_{S4,outer} = A_2 * \sin\left(2\pi f_1 * t + \frac{\pi}{2}\right).$$

The superposition of the magnetic fields generated by the coils of the one-sided coil assembly 12 driven with the above defined currents may then give rise to a field free line 28 rotating with the rotation frequency $f_1$ in said probe volume.

FIGS. 4C, 4D illustrate two top views (along the coil assembly axis 18) of a one-sided coil assembly 12 similar to the one illustrated in FIG. 2 including an illustration of a field free line 28 for two different exemplary current configurations.

In the first current configuration depicted in FIG. 4C, a current amplitude in the oppositely arranged coil assembly sectors 16a, 16c (top and bottom) is larger than a current amplitude in the oppositely arranged coil assembly sectors 16b, 16d (left and right), such that said field free line 28 is substantially aligned perpendicular to a connecting line between the coil assembly sectors 16a, 16c, or in other words extends substantially from the left side to the right side of the illustration.

In the second current configuration depicted in FIG. 4D, a current amplitude in the oppositely arranged coil assembly sectors 16a, 16c (top and bottom) has declined to a value similar to and slightly lower than a current amplitude in the oppositely arranged coil assembly sectors 16b, 16d (left and right), such that said field free line 28 is rotated with respect to the field free line 28 depicted in FIG. 4C and aligned substantially diagonally in the illustration. Thus, fully electric rotation of the field free line 28 may be obtained with the one-sided coil assembly 12 using said time varying currents with a periodic modulation associated with the rotation frequency $f_1$.

Based on the magnetic field directions close to the field free line 28 illustrated in FIGS. 3A, 3B, the skilled person will appreciate that said field free line 28 may further be translated perpendicular to the coil assembly axis 18 with a displacement field applied along the coil assembly axis 18, and may be translated along the direction of the coil assembly axis 18 by further applying a magnetic field perpendicular to a current extension direction of the field free line 28 and perpendicular to the coil assembly axis 18 at least close to the coil assembly axis 18.

Figure 5:
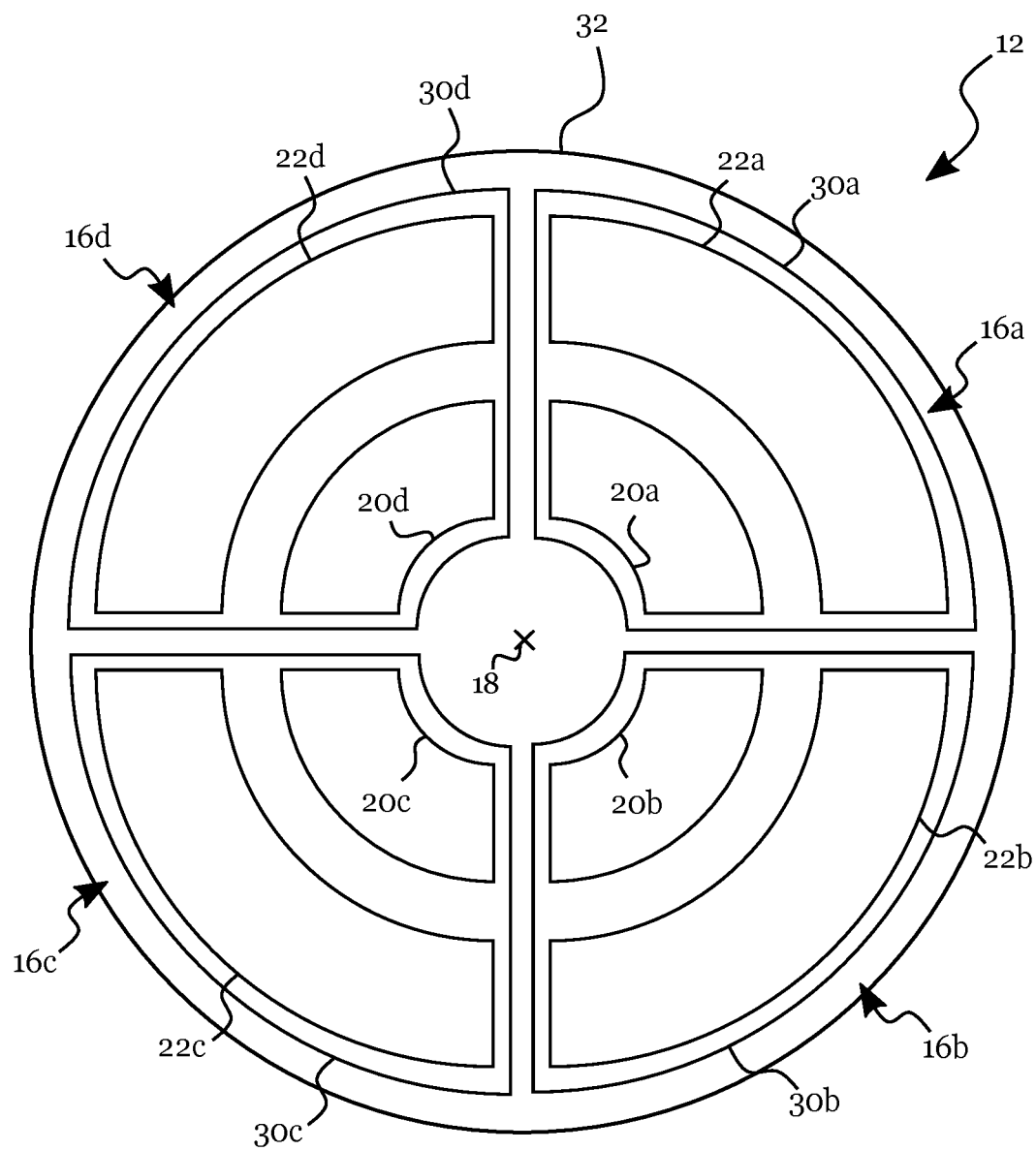
FIG. 5 illustrates a one-sided coil assembly comprising four height displacement coils and a dedicated radial displacement coil according to an example.

FIG. 5 illustrates a further one-sided coil assembly 12 according to an example comprising dedicated coils for the translation of the field free line 28 along two substantially perpendicular spatial directions. Said one-sided coil assembly 12 comprises in each of said circumferentially distributed coil assembly sectors 16a-d a respective height displacement coil 30a-d for generating a co-rotating magnetic field rotating in phase with the magnetic field distribution for defining the field free line 28, and further comprises a radial displacement coil 32 for generating a magnetic field aligned substantially along the coil assembly axis 18 for displacing the field free line 28 perpendicular to its extension direction and substantially perpendicular to the coil assembly axis 18 at least in a center of the one-sided coil assembly 12.

Said height displacement coils 30a-d are illustrated as coils having an annular shape and enclosing the inner coils 20a-d and the outer coils 22a-d of the respective coil assembly sectors 16a-d and may be driven with time varying currents comprising a modulation at the rotation frequency $f_1$ for generating a co-rotating magnetic field aligned substantially perpendicular to the current extension direction of the field free line 28. A field strength of said co-rotating magnetic field may then shift the field free line 28 up and down along the coil assembly axis 18.

Preferably, the rotation and the two translations movements of the field free line 28 along the substantially perpendicular displacement directions are generated with time varying currents comprising amplitude modulations at different frequencies for temporally separating the respective movements. For example, a frequency of radial displacement of the field free line 28 generated by modulating a current in the radial assessment coil with a radial displacement frequency $f_3$ may be higher than a frequency of rotation $f_1$ of the field free line 28, which may in turn be higher than a frequency of displacement $f_2$ of the field free line 28 along the coil assembly axis 18.

For example, each of the height displacement coils 30a-d in said coil assembly sectors S1-S4 may be driven with respective driving currents $I_{S1-S4,height}$ with a current amplitude $A_3$ and comprising a sinusoidal modulation with said height displacement frequency $f_2$, and further comprising a sinusoidal modulation associated with the rotation frequency $f_1$ and phase shifted between adjacent sectors S1-S4 by $\pi/2$:

$$I_{S1,height} = A_3 * \sin(2\pi f_2 * t) * \sin(2\pi f_1 * t);$$

$$I_{S2,height} = A_3 * \sin(2\pi f_2 * t) * \sin(2\pi f_1 * t + \pi/2);$$

$$I_{S3,height} = A_3 * \sin(2\pi f_2 * t) * \sin(2\pi f_1 * t + \pi);$$

$$I_{S4,height} = A_3 * \sin(2\pi f_2 * t) * \sin(2\pi f_1 * t + 3\pi/2);$$

while the radial displacement coil 32 may be driven with a time varying current $I_{radial}$ modulated with a sinusoidal modulation associated with a radial displacement frequency $f_3$ and a current amplitude $A_4$:

$$I_{radial} = A_4 * \sin(2\pi f_3 * t).$$

As a result, the field free line 28 may be rotated with the rotation frequency $f_1$, while concurrently being displaced along the coil assembly axis 18 with the height displacement frequency $f_2$, such as to perform a helical movement around the coil assembly axis 18. At the same time, the field free line 28 may be displaced along a radial direction aligned perpendicular to a current extension direction of the field free line 28 with the radial displacement frequency $f_3$, thereby providing three independent degrees of freedom for the state of the field free line 28 in order to scan the probe volume.

For example, said radial displacement may induce a displacement of the field free line 28 over a two-dimensional plane in the probe volume, wherein a magnetization of magnetic particles at the current position of the field free line 28 is inversed during the passage of the field free line 28 which may give rise to a nonlinear magnetization response to an excitation with the radial displacement frequency $f_3$. Said nonlinear response corresponds in each position of the field free line 28 to a parallel projection of the response of the magnetic particles along the current extension direction of the field free line 28, such that a position of magnetic particles in the investigated two-dimensional plane along said radial displacement direction may be encoded in the phase information of the response. Thus, by measuring said parallel protection of an investigated two-dimensional plane along a number of angles around the coil assembly axis 18, a spatial distribution of a response of magnetic particles in a two-dimensional slice of the probe volume may be determined. By shifting said two-dimensional slice along the coil assembly axis 18 with the height displacement frequency $f_2$ a response of said magnetic particles in the probe volume may be resolved along three dimensions.

FIGS. 6A-6C illustrate schematic side views of three different examples of using a plurality of one-sided coil assemblies 12a-d in order to concurrently scan associated probe volumes 34a-d located close to a facing surface of an extended sample S. For example, in FIG. 6A, said plurality of one-sided coil assemblies 12a-d are spaced perpendicular to the respective coil assembly axis 18 and face the same surface of the sample S to concurrently measure a presence of magnetic particles at or below said surface of the sample S. In FIG. 6B, a plurality of one-sided coil assemblies 12a-d are arranged to face different faces of an extended sample S (schematically depicted as an ellipse) to concurrently measure a presence of magnetic particles at said different faces from different orientations. In FIG. 6C a first coil assembly 12a and the second coil assembly 12b are arranged at opposite faces of a sample S to concurrently measure a presence of magnetic particles in a probe volumes 34a, 34b arranged at opposite sides of an extended sample S. Thus, said system 10 may be modular and comprise a plurality of one-sided coil assemblies 12a-d to parallelize a measurement of the presence of magnetic particles in probe volumes 34a-d associated with respective one-sided coil assemblies 12a-d.

In accordance with the example illustrated in FIG. 6A, a plurality of one-sided coil assemblies 12a-d may further be arranged in a lattice forming rows and columns of one-sided coil assemblies 12a-d, such as to provide a sensor array of one-sided coil assemblies 12a-d with associated probe volumes 34a, 34b spaced from a surface of the sensor array along its surface normal. Such an arrangement may be advantageously combined with miniaturized one-sided coil assemblies, which may be fabricated on a substrate using microfabrication techniques. For example, coil windings of one-sided coil assemblies may be fabricated on a sample by defining locations for current traces with photolithography, and by subsequently depositing a conductive material in selected subject portions, such as metal using e.g. sputtering, or by removing portions of a conductive layer on said substrate with a suitable etching process.

FIG. 7A illustrates an example of a one-sided coil assembly 12, wherein windings of the coils of said one-sided coil assembly 12 are arranged such as to allow placement of said windings in a common layer on a planar substrate. The illustrated one-sided coil assembly 12 comprises four circumferentially arranged planar coils 36a-d in corresponding coil assembly sectors 16a-d and a measurement coil 38 arranged in a center of the one-sided coil assembly 12 wherein a center of the measurement coil 38 is located close to the coil assembly axis 18. In other words, the planar coils 36a-d enclose the measurement coil 38 arranged in the center of the one-sided coil assembly 12. The windings of the illustrated planar coils 36a-d do not form a fully closed-loop but are connected to current feeds extending radially outward from the coil assembly axis 18 at the radially outward periphery of the one-sided coil assembly 12 (radially outward from the coil assembly axis 18).

As an example, the planar coils 36a-d may be driven with a time varying current comprising a periodic modulation associated with a rotation frequency $f_1$ wherein the time varying current is phase shifted between adjacent planar coils 36a-d by $\pi/2$, such as to generate a rotating magnetic field in a plane spaced from a top surface of the one-sided coil assembly 12 along the coil assembly axis 18. For example, the planar coils 36a-d may be driven with sinusoidally modulated time varying currents similar to the currents $I_{S1-S4,inner}/I_{S1-S4,outer}$ of the inner coils 20a-d/the outer coils 22a-d of the example described with reference to FIG. 4A-D. The current in the measurement coil 38 may then be measured as a function of a frequency and an amplitude of the time varying current in the planar coils 36a-d to measure a presence of magnetic particles in a probe volume spaced from the one-sided coil assembly 12 along the coil assembly axis 18 in accordance with rotational drift spectroscopy techniques.

Moreover, and as shown in FIG. 7B, a plurality of one-sided coil assemblies 12 may be arranged in rows R1-R4 and columns C1-C4 (separated by dashed lines for illustration) to form a sensor array 40 for concurrently measuring a presence of magnetic particles in a plurality of regularly spaced probe volumes associated with the respective one-sided coil assemblies 12. Such an array 40 of one-sided coil assembly 12 may be advantageously applied in biological research to detect a presence of magnetic nanoparticles functionalized as magnetic markers in a biological sample (not shown) located close to a surface of the sensor array 40. The skilled person will appreciate that the use of said one-sided coil assemblies 12 allows concurrent observation of the biological sample with a microscope for simultaneously obtaining optical images and measurements of the presence of magnetic particles in the regularly spaced probe volumes.

The preceding detailed description has focused mostly on the case of a one-sided coil assembly 12 comprising four circumferentially distributed coil assembly sectors 16a-d. However, the skilled person will appreciate that a one-sided coil assembly 12 may of also comprise only three circumferentially distributed coil assembly sectors 16a-c, which may e.g. each be accommodated in an angular range of 120° around the coil assembly axis 18, and which may be used to measure a presence of magnetic particles in a probe volume spaced from the one-sided coil assembly 12 along a central coil assembly axis 18. A one-sided coil assembly 12 comprising three circumferentially distributed coil assembly sectors 16a-c may increase a placement density of one-sided coil assemblies for a sensor array 40 as compared to the one-sided coil assemblies illustrated in FIG. 7B. Additionally, a one-sided coil assembly 12 may further comprise five or more circumferentially distributed coil assembly sectors 16a-d for additional control over a homogeneity of the magnetic field distribution during a rotation.

Moreover, the coils described herein have been illustrated schematically and in particular with only one respective winding per coil. However, the skilled person will further appreciate that for each coil a plurality of windings may be provided, as in a solenoid coil, and the plurality of windings may be arranged extending substantially along the coil assembly axis 18 to increase the field strengths generated by the coils of the one-sided coil assembly 12.

The description of the preferred embodiments and the figures merely serve to illustrate the invention and the beneficial effects associated therewith, but should not be understood to imply any limitation. The scope of the invention is to be determined solely by the appended claims.

LIST OF REFERENCE SIGNS 10 system
12 one-sided coil assembly
12a-d plurality of one-sided coil assemblies
14 current controller
16a-d coil assembly sectors
18 coil assembly axis
20a-d inner coils
22a-d outer coils
24 first point
26 second point
28 field free line
30a-d height displacement coils
32 radial displacement coil
34a-d associated probe volumes
36a-d circumferentially arranged planar coils
38 measurement coil
sensor array
S sample
$B_1, B_2$ magnetic field distribution

What is claimed is:

1. A system for measuring a presence of magnetic particles in a probe volume, said system comprising:
a coil assembly arranged around a central coil assembly axis for generating a rotating magnetic field distribution, said coil assembly comprising at least 3 circumferentially distributed coil assembly sectors, wherein said coil assembly sectors are arranged circumferentially with respect to said central coil assembly axis;
a current controller configured to generate a time varying current in each of said coil assembly sectors, said time varying current comprising a periodic modulation with a rotation frequency, wherein said periodic modulation is phase shifted between adjacent coil assembly sectors to generate a magnetic field rotating in a plane perpendicular to said central coil assembly axis, said magnetic field rotating with a rotation frequency associated with a frequency of said periodic modulation,
wherein said system is configured to measure said presence of magnetic particles in said probe volume with said coil assembly, wherein said coil assembly is configured such that the generated rotating magnetic field is spaced from the coil assembly along the central coil assembly axis in order for said probe volume to be spaced from said coil assembly along said central coil assembly axis.

2. The system of claim 1, wherein the coil assembly comprises a number of N circumferentially distributed coil assembly sectors, and wherein the periodic modulation is phase shifted between adjacent coil assembly sectors by an Nth part of a rotation period which is proportional to the inverse of said rotation frequency $f$.

3. The system of claim 1, wherein said circumferentially distributed coil assembly sectors are each arranged in a circular sector or in an annular sector, around said central coil assembly axis, and wherein said circular sectors or said annular sectors are uniformly distributed around said central coil assembly axis.

4. The system of claim 1, wherein each of the circumferentially distributed coil assembly sectors comprises an inner coil and an outer coil, a center of said inner coil being arranged closer to said central coil assembly axis than a center of the outer coil.

5. The system of claim 4, wherein a winding of said inner coil or of said outer coil comprises a pair of radially extending wires, an inner circumferentially extending wire and an outer circumferentially extending wire.

6. The system of claim 4, wherein the inner and the outer coil do not overlap when viewed along said central coil assembly axis.

7. The system of claim 4, wherein the magnetic field distribution comprises a field free line, and wherein said current controller is configured to drive the inner coil and the outer coil of each of said circumferentially distributed coil assembly sectors with counterrotating currents to generate
a first magnetic field aligned perpendicular to said central coil assembly axis at least in a first point on said central coil assembly axis, wherein the first magnetic field has a first orientation and is associated with the inner coils, and
a second magnetic field aligned perpendicular to said central coil assembly axis at least in a second point on said central coil assembly axis, wherein the second magnetic field has a second orientation, which is inverse to said first orientation, and is associated with the outer coils,
wherein said first point and said second point are spaced along said central coil assembly axis, and wherein said field free line is arranged between said first point and said second point.

8. The system of claim 7, wherein the current controller is further configured to generate a second time varying current in each of said coil assembly sectors, said second time varying current comprising the periodic modulation with the rotation frequency and being phase shifted between adjacent coil assembly sectors and further comprising a second periodic modulation with a height modulation frequency, to generate a co-rotating field component at least in a third point between said first point and said second point rotating with said rotating frequency, a field strength of said co-rotating field component being modulated with said height modulation frequency to shift said rotating field free line along said central coil assembly axis.

9. The system of claim 8, wherein the coil assembly comprises a height modulation coil in each of said circumferentially distributed coil assembly sectors, a center of said height modulation coil being farther from said central coil assembly axis than the center of said inner coil and being closer to said central coil assembly axis than the center of said outer coil.

10. The system of claim 7, wherein the current controller is further configured to generate a third time varying current in said coil assembly comprising a periodic modulation with a radial translation frequency to generate a magnetic field component along said central coil assembly axis in said probe volume to displace the field free line along a radial displacement direction with respect to said central coil assembly axis, said radial displacement direction being perpendicular to a current extension direction of the field free line.

11. The system of claim 1, wherein a top surface of the coil assembly facing the probe volume is flat or concave, wherein an angle between radially outward faces of the top surface and said central coil assembly axis is less than 45°.

12. The system of claim 1, further comprising a plurality of coil assemblies arranged in rows and columns to define rows and columns of a sensor array for measuring a presence of magnetic particles in a plurality of probe volumes of associated coil assemblies above said plurality of coil assemblies.

13. The system of claim 1, wherein the coil assembly is microscopic and has a radial extension perpendicular to said central coil assembly axis of less than 10 mm.

14. A method for measuring a presence of magnetic particles in a probe volume with a coil assembly arranged around a central coil assembly axis, wherein said probe volume is spaced from said coil assembly along said central coil assembly axis,
wherein said coil assembly comprises at least 3 circumferentially distributed coil assembly sectors, wherein said coil assembly sectors are arranged circumferentially with respect to said central coil assembly axis;
and wherein the method comprises:
generating a rotating magnetic field distribution by generating a time varying current in each of said coil assembly sectors, said time varying current comprising a periodic modulation, wherein said periodic modulation is phase shifted between adjacent coil assembly sectors to generate a magnetic field rotating in a plane perpendicular to said central coil assembly axis and spaced from the coil assembly along the central coil assembly axis in order for said probe volume to be spaced from said coil assembly along said central coil assembly axis, said magnetic field rotating with a rotation frequency associated with a frequency of said periodic modulation.

15. The method of claim 14, wherein the magnetic field distribution comprises a field free line, and wherein the method comprises:
driving an inner coil and an outer coil of each of said circumferentially distributed coil assembly sectors with counterrotating currents for generating
a first magnetic field aligned perpendicular to said central coil assembly axis at least in a first point on said central coil assembly axis, wherein the first magnetic field has a first orientation and is associated with the inner coils, and
a second magnetic field aligned perpendicular to said central coil assembly axis at least in a second point on said central coil assembly axis, wherein the second magnetic field has a second orientation, which is inverse to said first orientation, and is associated with the outer coils,
wherein said first point and said second point are spaced along said central coil assembly axis, and wherein said field free line is arranged between said first point and said second point.

16. The method of claim 14, further comprising:
generating a second time varying current in each of said coil assembly sectors, said second time varying current comprising the periodic modulation with the rotation frequency and being phase shifted between adjacent coil assembly sectors and further comprising a second periodic modulation with a height modulation frequency, for generating a co-rotating field component at least in a third point between said first point and said second point rotating with said rotating frequency, a field strength of said co-rotating field component being modulated with said height modulation frequency to shift said rotating field free line along said central coil assembly axis,
wherein the coil assembly comprises a height modulation coil in each of said circumferentially distributed coil assembly sectors, a center of said height modulation coil being farther from said central coil assembly axis than a center of said inner coil and being closer to said central coil assembly axis than a center of said outer coil, and wherein the method comprises:
applying said second time varying current to said height modulation coil.

17. The method of claim 14, further comprising:
generating a third time varying current in said coil assembly comprising a periodic modulation with a radial translation frequency for generating a magnetic field component along said central coil assembly axis in said probe volume for displacing the field free line along a radial displacement direction with respect to said central coil assembly axis, said radial displacement direction being perpendicular to a current extension direction of the field free line, and wherein the method comprises:
applying said third time varying current to said radial displacement coil.

18. The method of claim 14, further comprising:
providing a plurality of coil assemblies arranged in rows and columns to define rows and columns of a sensor array for measuring a presence of magnetic particles in a plurality of probe volumes of associated coil assemblies above said plurality of coil assemblies.

19. The method of claim 18, further comprising:
driving each of said coil assemblies with said time varying current.

20. A non-transitory computer-readable medium storing computer readable instructions that, when executed by a processing unit cause the processing unit to implement a method of measuring a presence of magnetic particles in a probe volume with a coil assembly arranged around a central coil assembly axis, wherein said probe volume is spaced from of the coil assembly along said central coil assembly axis, and wherein said coil assembly comprises at least 3 circumferentially distributed coil assembly sectors, wherein said coil assembly sectors are arranged circumferentially with respect to said central coil assembly axis with the steps of:
generating a rotating magnetic field distribution by generating a time varying current in each of said coil assembly sectors, said time varying current comprising a periodic modulation, wherein said periodic modulation is phase shifted between adjacent coil assembly sectors to generate a magnetic field rotating in a plane perpendicular to said central coil assembly axis and spaced from the coil assembly along the central coil assembly axis in order for said probe volume to be spaced from said coil assembly along said central coil assembly axis, said magnetic field rotating with a rotation frequency associated with a frequency of said periodic modulation.

\* \* \* \* \*

UNITED STATES PATENT AND TRADEMARK OFFICE
CERTIFICATE OF CORRECTION

Page 1 of 1

PATENT NO. : 11,927,651 B2
APPLICATION NO. : 17/431962
DATED : March 12, 2024
INVENTOR(S) : Patrick Vogel It is certified that error appears in the above-identified patent and that said Letters Patent is hereby corrected as shown below:

In the Specification

Under RELATED APPLICATION paragraph, delete "PCT/EP2020/054548" and insert --PCT/EP2020/054584--.

Signed and Sealed this
Sixteenth Day of April, 2024

Katherine Kelly Vidal
*Director of the United States Patent and Trademark Office*